United States Patent [19]

Saari

[11] Patent Number: 4,880,821
[45] Date of Patent: Nov. 14, 1989

[54] α-NITROALKYLNITROBENZENESULFONAMIDES

[75] Inventor: Walfred S. Saari, Lansdale, Pa.

[73] Assignee: Merck & Co., Inc., Rahway, N.J.

[21] Appl. No.: 233,316

[22] Filed: Aug. 17, 1988

[51] Int. Cl.⁴ ............... A61K 31/445; A61K 31/18; C07D 211/06; C07C 143/80
[52] U.S. Cl. ................... 514/331; 514/603; 514/216; 514/428; 514/187; 514/210; 564/87; 546/232; 548/950; 548/967; 548/569; 540/604; 540/482
[58] Field of Search ............ 564/87; 546/232; 514/603, 331, 212, 428, 183, 210; 540/604, 482; 548/950, 967

[56] References Cited

U.S. PATENT DOCUMENTS 4,603,133  7/1986  Engelhardt et al. ............ 514/229
4,731,369  3/1988  Engelhardt et el. ............ 514/327

OTHER PUBLICATIONS

Coleman, *Journal of the National Cancer Institute*, vol. 80, no. 5 pp. 310–317 (1988).

*Primary Examiner*—Richard L. Raymond
*Assistant Examiner*—Mark W. Russell
*Attorney, Agent, or Firm*—Richard S. Parr; Michael C. Sudol

[57] ABSTRACT

A compound of the formula

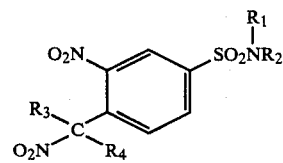

wherein:
$R_1$ and $R_2$ are defined as follows:
$R_1$ is hydrogen, an alkyl group, or an alkyl group having one or more hydroxy groups;
$R_2$ is an alkyl group having one or more hydroxy groups, or an alkyl group containing an amino group in which the amino function is substituted with hydrogen or one or two individual alkyl groups same or different, or two alkyl groups which together form a cyclic amine, e.g. piperidine;
$R_3$ is hydrogen or an alkyl group; and
$R_4$ is hydrogen or an alkyl group.

The compounds have high radiosensitizing activity and selectivity for hypoxic cells.

9 Claims, No Drawings

α-NITROALKYLNITROBENZENESULFONA-MIDES

BACKGROUND OF THE INVENTION

The invention relates to hypoxic cell radiation sensitizers that have high radiosensitizing activity and selectivity for hypoxic cells.

Hypoxic cells are relatively resistant to killing by radiation. To achieve the same proportion of cell kill, about three times the radiation dose is required as for well oxygenated cells. Oxygen has the ability to sensitize cells to ionizing radiation at clinically useful radiation doses. Coleman, *Journal of the National Cancer Institute* Vol. 80, No. 5 pp. 310-317 (1988) describes hypoxia in tumors and various approaches to treatment of hypoxic cells.

U.S. Pat. No. 4,603,133 relates to esters, amides and N-substituted amides of 2-[N-(morpholinoalkyl-)aminosulfonyl]-6-nitrobenzoic acids, used as sensitizers of hypoxic tumor cells to therapeutic radiation. That patent also relates to 2-chlorosulfonyl-6-nitrobenzoate ester prepared as described in U.S. Ser. No. 716,886 filed March 27, 1985 and aminating said 2-chlorosulfonylbenzoate ester to produce the corresponding sulfamyl or N-substituted sulfamylnitrobenzoic esters.

U.S. Ser. No. 937,275, filed Dec. 3, 1986, describes 3-nitrobenzenesulfonamides useful in enhancing the effect of therapeutic radiation.

U.S. Ser. No. 937,277, filed Dec. 3, 1986, describes 2-(substituted sulfamyl) derivatives of 4-nitrobenzamide useful for increasing the sensitivity of hypoxic cancer cells to X-rays and gamma-radiation.

U.S. Pat. No. 4,731,369 describes amides and esters of 2-(N-(hydroxypiperidinoalkyl) and (hydroxypyrrolidinoalkyl)-aminosulfonyl)-6-nitrobenzoic acids which are useful for treating patients in need of therapeutic radiation.

DETAILED DESCRIPTION OF THE INVENTION

The compounds of the present invention are of the following formula:

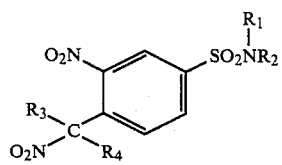

$R_1$ and $R_2$ are defined as follows:

$R_1$ is hydrogen, an alkyl group, or an alkyl group having one or more hydroxy groups;

$R_2$ is an alkyl group having one or more hydroxy groups, or an alkyl group containing an amino group in which the amino function is substituted with hydrogen or one or two individual alkyl groups same or different, or two alkyl groups which together form a cyclic amine, e.g. piperidine;

$R_3$ is hydrogen or an alkyl group; and $R_4$ is hydrogen or an alkyl group.

Compounds of the invention are electron-acceptors which form radical anions in the reducing environment of hypoxic cells or upon irradiation and from which nitrite is released. The $S_{RN}1$ mechanism by which these compounds release nitrite is completely inhibited by molecular oxygen, and offers unique opportunities for the selective release of anions in hypoxic environments.

The $S_{RN}1$ mechanism is a radical chain mechanism which can be initiated by generation of a radical anion. It leads to the nucleophilic substitution of benzylic groups, Y for X in the following sequence:

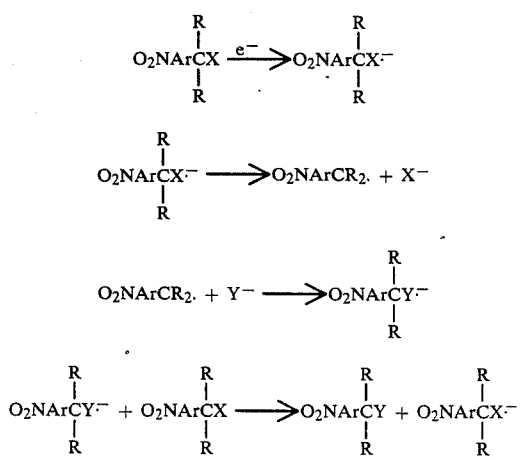

Compounds of the invention are selective radiosensitizers of hypoxic cells. The release of nitrite from the radical anion through an $S_{RN}1$ mechanism takes place under hypoxic conditions. Loss of nitrite by SN2 displacement is difficult due to the α-nitroisopropyl group, and the electronegative nature of the aromatic ring discourages SN1 reactions. In addition, the radical resulting from nitrite elimination possesses alkylating potential and will react with sulphydryl or other cellular constituents.

One preferred compound of the present invention is:

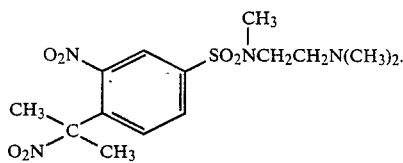

Another preferred compound of the present invention is:

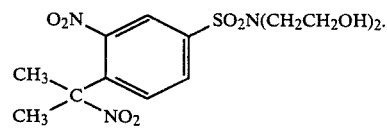

Procedures for synthesis of these compounds, as well as other compounds of the present invention, are presented below.

The method of treatment of human patients or domestic animals undergoing radiation treatment of malignant disease processes employs the compounds of the present invention in pharmaceutical compositions that are administered orally or intravenously or in depot formulations.

When the compounds are used in conjunction with radiation treatments, the dose employed depends on the radiation protocol for each individual patient. They can be administered from 10 minutes to 5 hours prior to the radiation treatment in a dose of from 0.25 to 4.0 grams per square meter of body surface. The compounds may be employed at intervals during a multi-fraction protocol, and not necessarily with each treatment.

When the compounds are used as cytotoxic agents to hypoxic cells, they can be administered daily in divided doses up to 0.25 to 4.0 grams per square meter of body surface.

The dosage range given is the effective dosage range and the decision as to the exact dosage used must be made by the administering physician based on his judgement of the patient's general physical condition. In determining the dose for the individual patient, the physician may begin with an initial dose of 0,25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs may also be used.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention. Temperatures are in degrees Celsius unless otherwise indicated throughout the application.

EXAMPLES

EXAMPLE 1

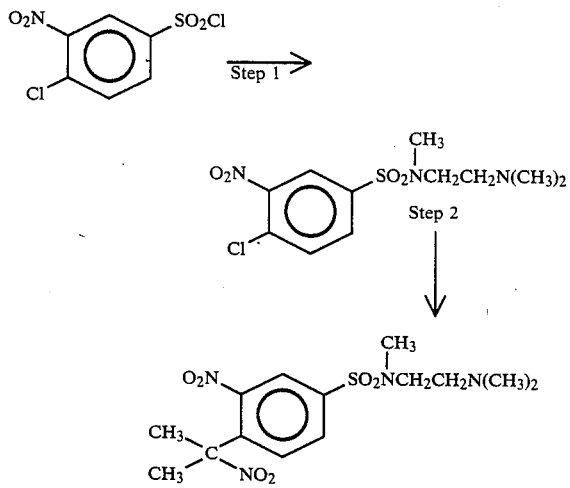

Step 1:
N-(2-Dimethylaminoethyl)-N-methyl-4-chloro-3-nitrobenzenesulfonamide hydrochloride A solution of N,N,N'-trimethylethylenediamine (4.96 mL, 39 mmol) and N,N-diisopropylethylamine (6.79 mL, 39 mmol) in tetrahydrofuran (150 mL) was added over 30 minutes to a stirred, cooled solution of 4-chloro-3-nitrobenzenesulfonyl chloride (10 g, 39 mmol) in tetrahydrofuran (100 mL). After addition was complete, the reaction mixture was stirred in the ice bath for 1 hour, at 20°–25° for 2 hours and then concentrated under reduced pressure. After partitioning between ethyl acetate and water, the ethyl acetate extract was washed with a saturated aqueous solution of sodium chloride, dried ($Na_2SO_4$), filtered and concentrated. The residue was treated with anhydrous ethanolic hydrogen chloride and the salt recrystallized from methanol ethyl acetate to give the hydrochloride salt (10.2 g, 73%), m.p. 227°–30° dec.

Anal Calcd. for $C_{11}H_{16}ClN_3O_4S \cdot HCl$:
C, 36.88; H, 4.78; N, 11.73.
Found: C, 36.68; H, 4.58; N, 12.08.

Step 2:
N-(-2-Dimethylaminoethyl)-N-methyl-4-(1-methyl-1-nitro1-ethyl)-3-nitrobenzenesulfonamide hydrochloride A solution of N-(2-dimethylaminoethyl)-N-methyl-4-chloro-3-nitrobenzenesulfonamide base (15.65 g, 49 mmol) and the lithium salt of 2-nitropropane (4.66 g, 49 mmol) in dimethylsulfoxide (100 mL) was stirred under nitrogen at 20°–25° for 3 days. An additional 0.35 g of the lithium salt was then added and stirring continued for three days more. After pouring the reaction mixture on ice, product was extracted into a 1:1 mixture of ethyl acetate and toluene which was washed with water, dried ($Na_2SO_4$), filtered and concentrated. Flash chromatography of the residue over silica gel and elution with 3% methanol-97% methylene chloride afforded 2.0 g of product. Treatment with anhydrous ethanolic hydrogen chloride and recrystallization from methanol-ethyl acetate hexane gave the hydrochloride salt, m.p. 231°–32.5° dec.

Anal. Calcd. for $C_{14}H_{22}N_4O_6S$ HCl:
C, 40.92, H, 5.64; N, 13.64.
Found: C, 41.24; H, 5.86; N, 14.03.

Nitrite Release from Electrolytic Reduction.

A 0.01 mM sample in 5 mL of 0.1 M tetrabutylammonium perchlorate - DMF solution was electrolyzed with D.C. polarography at a mercury electrode (vs Ag/AgCl) under argon. Immediately after electrolysis for 4–5 minutes, one mL of the resulting solution was added to the supporting electrolyte, 4 mL of an aqueous solution (ph 2–3) of diphenylamine, NaSCN and perchloric acid. Released nitrite was determined by differential pulse polarography under conditions where the test compound did not release nitrite. Nitrite concentration was determined by comparison of peak current with calibration curves. The method of standard additions was also used to insure accuracy.

Upon electrolytic reductions for 4-5 minutes in DMF,N-(2dimethylaminoethyl)-N methyl 4-(1-methyl-1nitro-1-ethyl)-3nitrobenzenesulfonamide hydrochloride released 92.9% of the theoretically available nitrite. The compound was stable under oxic conditions.

EXAMPLE 2

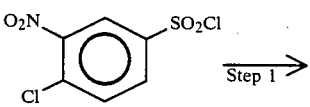

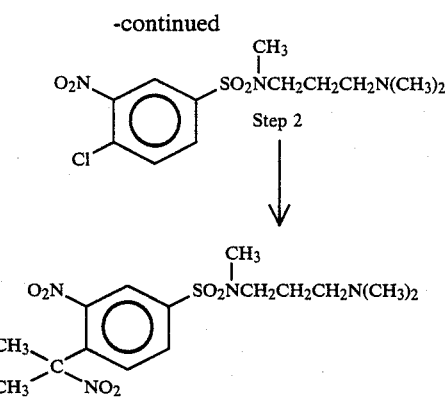

Step 1:
N-(3Dimethylaminopropyl)-N-methyl-4-chloro-3-nitrobenzenesulfonamide hydrochloride Reaction of 4-chloro-3-nitrobenzenesulfonyl chloride with N,N,N'-trimethylpropylenediamine in tetrahydrofuran by the procedure of Step 1, Example 1 gave N-(3-dimethylaminopropyl)-N-methyl-4- chloro-3-nitrobenzenesulfonamide hydrochloride.

Step 2:
N-(3-Dimethylaminopropyl)-N-methyl-4-(1-methyl-1-nitro-1-ethyl)-3-nitrobenzenesulfonamide hydrochloride A solution of N-(3-dimethylaminopropyl)-N-methyl-4-chloro-3-nitrobenzenesulfonamide and the lithium salt of 2-nitropropane in dimethylsulfoxide was stirred at 20°–25° C. for 2 days. The reaction was processed by the procedure of Step 2, Example 1 to give the hydrochloride salt.

EXAMPLE 3

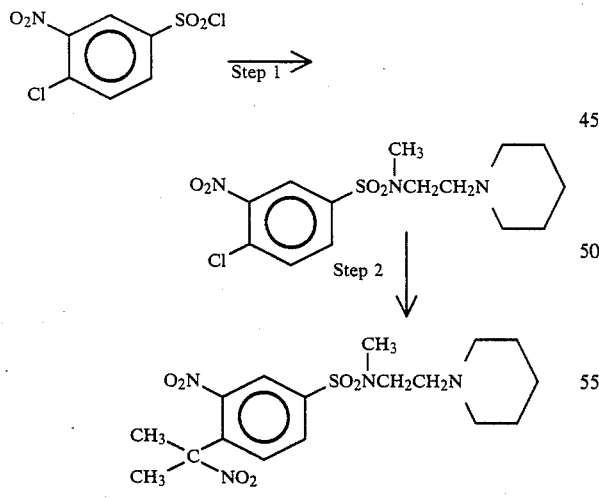

Step 1
N-Methyl-N-(2-piperidinoethyl)-4-chloro-3-nitrobenzenesulfanomide hydrochloride Reaction of 4-chloro-3-nitrobenzenesulfonylchloride with N-(2-methylaminoethyl)piperidine in tetrahydrofuran by the procedure of Step 1, Example 1 gave the corresponding N-(2-piperidino ethyl) derivative.

Step 2 N-Methyl-N (2-piperidinoethyl)-4-(1-methyl-1-nitro-1-ethyl)-3-nitrobenzenesulfonamide hydrochloride An equimolar solution of the chloro derivative of Step 1 and the lithium salt of 2-nitropropane in dimethylsulfoxide was stirred at 20°–25° for 3 days. The reaction was worked up by the procedure of Step 2, Example 1 to give the hydrochloride salt of the N-(2-piperidinoethyl) derivative.

It was found that p-nitrophenoxy is a better leaving group than chloro in displacement reactions of lithio 2-nitropropane. Compounds of the invention prepared using p-nitrophenoxy as a leaving group are shown in Examples 4–6.

EXAMPLE 4

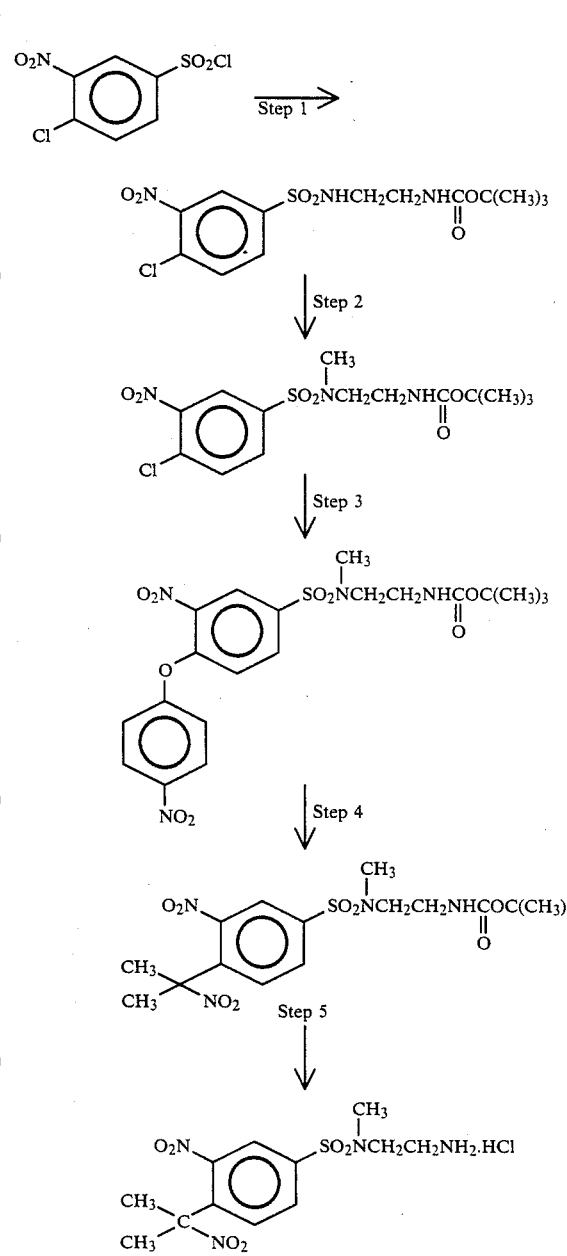

Step 1: N-(2-tert Butoxycarbonylaminoethyl)-4-chloro-3-nitrobenzenesulfanomide A solution of N-(2-aminoethyl) tert butoxycarbamate (3.86 g, 24.1 mmol) and N,N-diisopropylethylamine (4.2 mL, 24.1 mmol) in tetrahydrofuran (50 mL) was added over 1 hour to a stirred, cooled solution of 4-chloro-3-nitrobenzenesulfonyl chloride (6.17 g, 24.1 mmol) in tetrahydrofuran (50 mL). After addition was complete, the reaction mixture was stirred at 20°–25° for 20 hours and then concentrated under reduced pressure. The residue was partitioned between ethyl acetate and water and the ethyl acetate extract washed with brine, dried (Na$_2$SO$_4$), filtered and concentrated. Flash chromatography of the residue over silica gel and elution with a 2% methanol-98% chloroform mixture gave 6.3 g (68.9%) of pure product. An analytical sample, mp 130°–132°, soften at 114°, was obtained upon recrystallization from ethyl acetate-hexane.

Anal. cald'd for C$_{13}$H$_{18}$ClN$_3$O$_6$S: C, 41.11; H, 4.78; N, 11.06.

Found: C, 41 38; H, 4.88; N, 11.19

Step 2: N-(2-tert.Butoxycarbonylaminoethyl)-N-methyl-4-chloro-3- nitrobenzenesulfonamide Dimethylsulfate (1.4 mL, 15 mmol) was added over 30 minutes to a stirred solution of N-(2- tert.-butoxycarbonylaminoethyl)-4-chloro-3- nitrobenzenesulfonamide (2.44 g, 6.42 mmol) in methanol (20 mL) containing water (10 mL) and 10% sodium hydroxide solution (6 mL). After stirring at 20°–25° for 3 hours, the reaction mixture was diluted with water and ethyl acetate and the pH adjusted to 9-10 with 10% sodium hydroxide solution. The ethyl acetate layer was washed with brine, dried (Na$_2$SO$_4$), filtered and concentrated. Flash chromatography of the residue over silica gel and elution with chloroform afforded 1.6 g (63.2%) cf product mp 115.0°–117.5°. An analytical sample, mp 119.5°–121.5°, was obtained upon recrystallization from ethyl acetate-hexane.

Anal. calc'd. for C$_{14}$H$_{20}$ClN$_3$O$_6$S: C, 42.69; H, 5.12; N, 10.67.

Found: C, 42.91; H, 5.23; N, 10.63.

Step 3: N-(2tert.Butoxycarbonylaminoethyl)-N-methyl-4-(4-nitrophenoxy)-3-nitrobenzenesulfonamide To a solution of N-(2tert.butoxycarbonylaminoethyl)-N-methyl-4-chloro-3-nitrobenzenesulfon amide (1.5 g, 3.81 mmol) and 4-nitrophenol (0.53 g, 3.81 mmol) in dimethylformamide (30 mL) was added 60% sodium hydride-mineral oil suspension (0.15 g, 3.81 mmol). The resulting solution was stirred at 20°–25° under nitrogen for 3 days. After concentrating under reduced pressure at 55°, the residue was partitioned between ethyl acetate and 1 M acetic acid. The ethyl acetate extract was washed with sodium bicarbonate solution, brine and dried (Na$_2$SO$_4$). After filtering and concentrating under reduced pressure, the residue was flash chromatographed over silica gel. Elution with chloroform gave 2.0 g of the 4 nitrophenyl ether containing some unreacted chloro compound.

Step 4: N-(2-tert.Butoxycarbonylaminoethyl)-N-methyl-4-(1-methyl-1-nitro-1-ethyl)-3-nitrobenzene sulfonamide Solid 2- lithio- 2-nitropropane (0.48 g, 5.04 mmol) was added to a solution of 1.0 g of the 4-nitrophenyl ether from Step 3 in dimethylsulfoxide (15 mL) and the solution stirred at 20°–25° for 1 day. The reaction mixture was poured on ice and crude product extracted into ethyl acetate which was washed with brine. After drying (Na$_2$SO$_4$), filtering and concentrating, the residue was flash chromatographed over silica gel. Elution with chloroform gave 0.2 g of product as a yellow oil.

Step 5: N-(2-Aminoethyl)-N methyl-4-(1-methyl-1-nitro-1-ethyl)-3-nitrobenzenesulfonamide Hydrochloride A solution of the BOC protected amine of Step 4 (0.2 g) in ethyl acetate (15 mL) was cooled in an ice bath and saturated with hydrogen chloride gas over 5 minutes. After warming to 20°–25° over 45 minutes, solvent was removed under reduced pressure and the residue recrystallized from methanol-ethyl acetate hexane to give 0.16 g of analytically pure product, mp 207.5°–209.5° dec.

Anal. calc'd for C$_{12}$H$_{18}$H$_4$O$_6$S HCl: C, 37.65; H, 5.00, N, 14.64.

Found: C, 37.80; H, 4.97; N, 14.49.

EXAMPLE 5

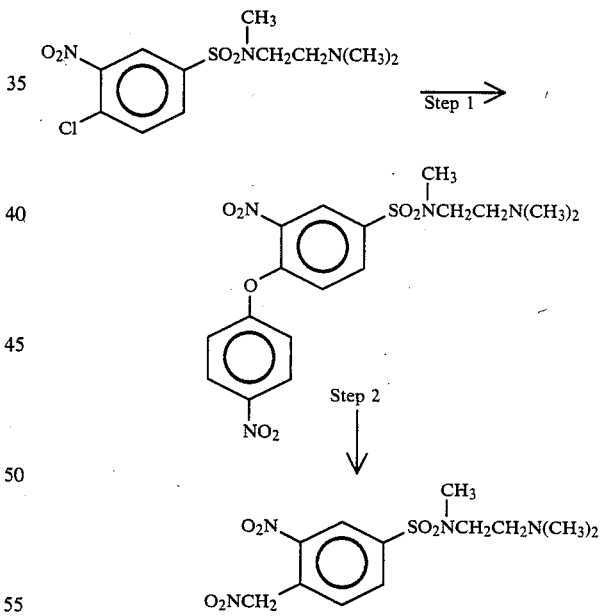

Step 1: N-(2-Dimethylaminoethyl)-N-methyl-4-(4-nitrophenoxy)-3-nitrobenzenesulfonamide To a solution of N-(2- dimethylaminoethyl)-N-methyl-4- chloro-3-nitrobenzenesulfonamide (2.2 g, 6.84 mmol) and 4- nitrophenol (0.97 g, 7.0 mmol) in dimethylformamide (30 mL) was added 60% sodium hydride-mineral oil suspension (0.28 g, 7.0 mmol). The resulting solution was stirred at 60° for 20 hours under N$_2$. After concentrating under reduced pressure at 50°, the residue was partitioned between ethyl acetate and water.

The ethyl acetate extract was washed with brine, dried (Na₂SO₄), filtered and concentrated. The residue was flash chromatographed over silica gel and 2.8 g of the nitrophenyl ether eluted with 3% methanol-97% chloroform.

Step 2:
N-(2-Dimethylaminoethyl)-N-methyl-4-(1-nitromethyl)-3-nitrobenzenesulfonamide Hydrochloride To a solution of nitromethane (0.37 g, 6.02 mmol) in dimethylsulfoxide (10 mL) at 20°-25° was added under nitrogen, 60% sodium hydride mineral oil suspension (0.24 g, 6.02 mmol). When all of the sodium hydride had reacted, a solution of the nitrophenyl ether from Step 1 (1.28 g, 3.01 mmol) in dimethylsulfoxide (5 mL) was added. The reaction mixture was stirred at 20°-25° for 2 days and then diluted with 1 M acetic acid (20 mL) and glacial acetic acid (2 mL). After adding excess saturated sodium bicarbonate solution, the product was extracted into ethyl acetate, washed with brine, dried (Na₂SO₄), filtered and concentrated. Flash chromatography over silica gel and elution with 5% methanol-95% chloroform gave the nitromethyl derivative.

EXAMPLE 6 stirred, cooled solution of 4-chloro-3-nitro benzenesulfonylchloride (10.0 g, 39 mmol) in tetrahydrofuran (100 mL). After addition was complete, the reaction mixture was stirred in the ice bath for 1 hour, 20°-25° for 5 hours, and then concentrated under reduced pressure. The residue was partitioned between ethyl acetate and water and the ethyl acetate extract washed with brine, dried (Na₂SO₄), filtered and concentrated. Flash chromatography of the residue over silica gel and elution with 5% methanol-95% chloroform gave 9.0 g of solid, mp 100°-102°. An analytical sample with the same mp was obtained upon recrystallization from ethyl acetate-hexane.

Anal. Calc'd. for $C_{10}H_{13}ClN_2O_6S$: C, 36.98; H, 4.03; N, 8.63.
Found: C, 36.92; H, 4.03; N, 8.65.

Step 2.
N,N-Bis[2-(2-tetrahydropyranyl)ethyl]-4-chloro-3-nitro benzenesulfonamide A solution of N,N-di(2-hydroxyethyl)-4-chloro-3-nitrobenzenesulfonamide (7.1 g, 21.9 mmol), 3,4-dihydro-2H-pyran (4.4 mL, 48 mmol) and p-toluenesulfonic acid hydrate (0.10 g) in methylene chloride (200 mL) was stirred at 20°-25° for 3 days. After washing with a

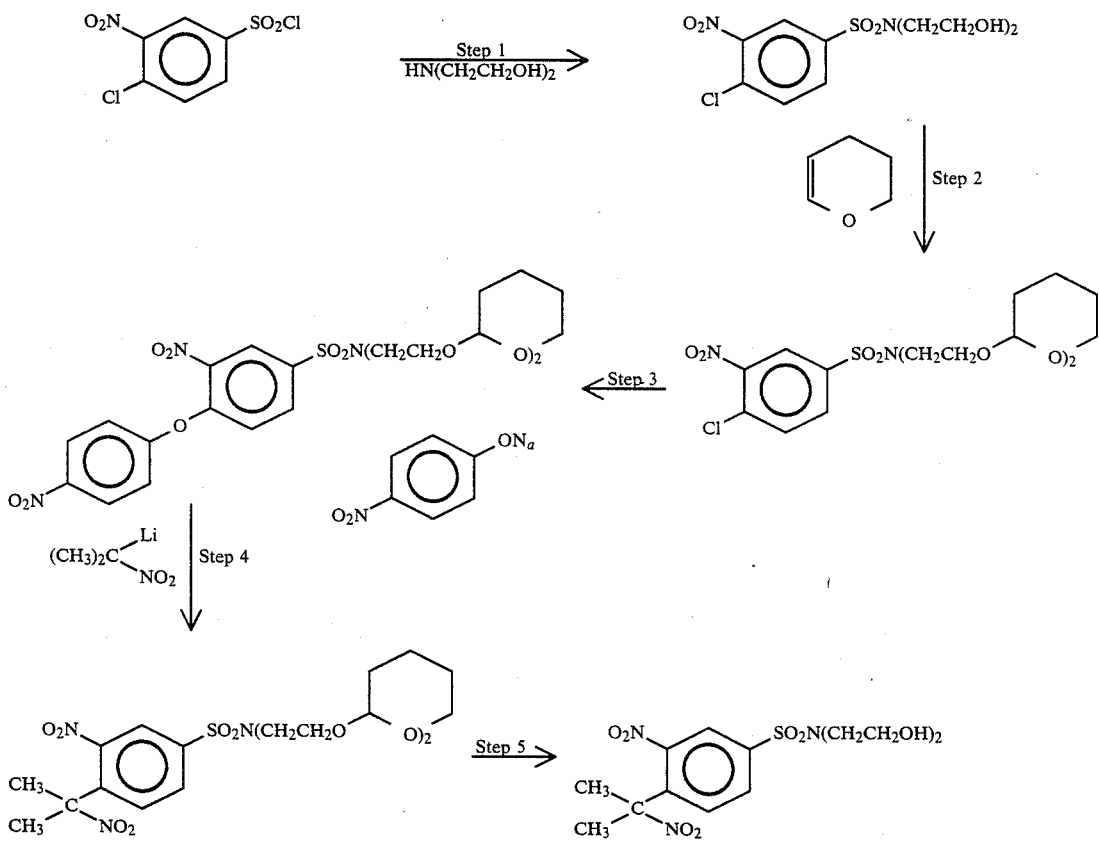

N,N-Di(2-hydroxyethyl)-4-(1-methyl-1-nitro-1-ethyl)-3-nitro benzenesulfanomide

Step 1.
N,N-Di(2-hydroxyethyl)-4-chloro-3-nitrobenzenesulfonamide

A solution of diethanolamine (3.7 mL, 39 mmol) and N,N-diisopropylethylamine (6.8 mL, 39 mmol) in tetrahydrofuran (100 mL) was added over 30 minutes to a saturated solution of sodium bicarbonate the organic layer was dried (Na₂SO₄), filtered and concentrated. Flash chromatography of the residue over silica gel with chloroform gave 9.0 g of product.

Step 3. N,N Bis[2-(2-tetrahydropyranyl)ethyl]-4-chloro-3-(4-nitrophenoxy) benzenesulfonamide To a solution of the chloro derivative from Step 2 (6.5 g, 13.2 mmol) and p-nitrophenol (1.95 g, 14.0 mmol) in dimethylformamide (75 mL) was added 60% sodium hydride mineral oil suspension (0.56 g, 14.0 mmol). The resulting solution was stirred at 60° under nitrogen for 19 hours. After concentrating under reduced pressure at 60°, the residue was partitioned between ethyl acetate and brine. The organic extract was dried ($Na_2SO_4$) filtered and concentrated. The residue was flash chromatographed over silica gel and 6.8 g of pure product was eluted with 15% ethyl acetate - 85% n-butylchloride.

Step 4. N,N-Bis[2-(2-tetrahydropyranyl)ethyl]-4-(1-methyl-1-nitro-1-ethyl)-3-nitrobenzene sulfonamide Solid 2-lithio-2-nitropropane (1.69 g, 17.8 mmol) was added to a solution of the nitrophenyl ether from Step 3.(5.3 g, 8.90 mmol) in hexamethyl phosphoramide (40 mL) and the solution stirred at 20°-25° C. for 1 day. The reaction mixture was then poured into ice water and the crude product extracted into ethyl acetate. After washing with brine, drying ($Na_2SO_4$), filtering and concentrating, the residue was flash chromatographed on silica gel. Elution with 25% ethyl acetate-75% n-butylchloride gave 2.6 g of pure product.

Step 5. N,N-Di(2-hydroxyethyl)-4-(1-methyl-1-nitro-1-ethyl)-3-nitrobenzenesulfonamide A solution of the tetrahydropyranyl ether of Step 4 (2.95 g) in tetrahydrofuran (200 mL), water (100 mL) and glacial acetic acid (300 mL) was stirred at 50° for 20 hours. After concentrating under reduced pressure, the residue was dissolved in ethyl acetate which was then washed with a saturated solution of sodium bicarbonate and brine. The ethyl acetate extract was dried ($Na_2SO_4$), filtered and concentrated and the residue flash chromatographed over silica gel. Elution with 3% methanol-97% chloroform and recrystallization from ethyl acetate-hexane gave 1.3 g or analytically pure product, mp 109.0°-110.5°.

Anal. Calc'd. for $C_{13}H_{19}N_3O_8S$: C, 41.37; H, 5.07; N, 11.13.
Found: C, 41.45; H, 5.02; N, 11.02.

What is claimed is:

1. A compound of the formula:

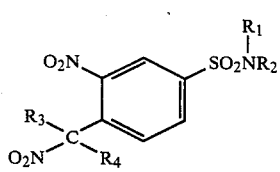

wherein:
$R_1$ and $R_2$ are defined as follows:
$R_1$ is hydrogen, an alkyl group, or an alkyl group having one or more hydroxy groups;
$R_2$ is an alkyl group having one or more hydroxy groups, or an amino group in which the amino function is substituted with hydrogen or one or two individual alkyl groups same or different, or two alkyl groups which together form a cyclic amine;
$R_3$ is hydrogen or an alkyl group; and
$R_4$ is hydrogen or an alkyl group.

2. A compound of claim 1 wherein $R_1$ and $R_2$ are alkyl groups having one or more hydroxy groups.

3. A compound of claim 1 where $R_2$ is an aminoalkyl group.

4. The compound of claim 2 which is:

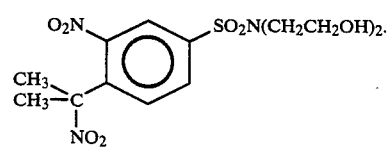

5. The compound of claim 3 which is:

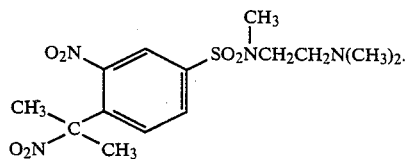

6. The compound of claim 3 which is:

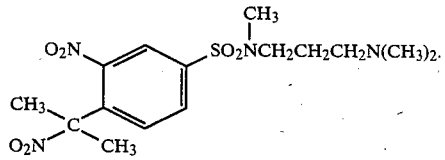

7. The compound of claim 3 which is:

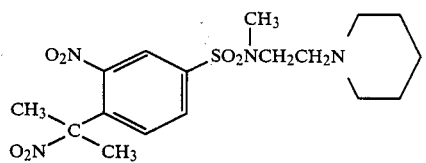

8. The compound of claim 3 which is:

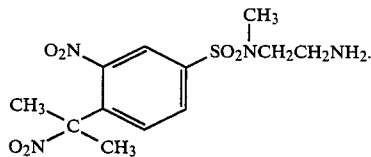

9. A pharmaceutical composition for enhancing the therapeutic effect of radiation which consists of an effective amount of a compound defined in claim 1 and a non-toxic pharmaceutically acceptable carrier.

* * * * *